United States Patent
Bonne et al.

(10) Patent No.: US 7,127,935 B2
(45) Date of Patent: Oct. 31, 2006

(54) WIRELESS GAS COMPOSITION SENSOR SYSTEM

(75) Inventors: Ulrich Bonne, Hopkins, MN (US); Rajiv R. Singh, Getzville, NY (US); Syed M. Shahed, Rancho Palos Verdes, CA (US); Richard A. Kirkpatrick, II, Richardson, TX (US); Aziz Rahman, Sharon, MA (US); Yue Liu, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/053,569

(22) Filed: Feb. 7, 2005

(65) Prior Publication Data

US 2006/0174692 A1 Aug. 10, 2006

(51) Int. Cl.
*G01N 7/00* (2006.01)
*G01N 33/00* (2006.01)
(52) U.S. Cl. .................. 73/23.2; 73/23.31; 73/31.05; 257/253
(58) Field of Classification Search .............. 73/23.2, 73/23.31, 23.32, 31.05, 31.06; 257/253
See application file for complete search history.

(56) References Cited

U.S. PATENT DOCUMENTS 6,340,864 B1 * 1/2002 Wacyk .................. 315/158
2004/0159142 A1 * 8/2004 Knott et al. .............. 73/23.32
2004/0218175 A1 * 11/2004 Barkhoudarian et al. ... 356/326
2005/0285155 A1 * 12/2005 Johnson et al. ............ 257/253

FOREIGN PATENT DOCUMENTS

JP 2000179847 A * 6/2000

OTHER PUBLICATIONS

JP 2000179847 A English language machine translation from JP Patent Office and Derwent English language abstract.*

* cited by examiner

*Primary Examiner*—Daniel S. Larkin
(74) *Attorney, Agent, or Firm*—Kris T. Fredrick

(57) ABSTRACT

A sensor system for detecting the presence of at least one specific component in a fluid medium such as an exhaust gas. A sensor is mounted in a sensor body for detecting the presence of at least one specific component and providing a representative signal that is transmitted to a remote receiver for processing. A power source such as a thermopile provides power for the sensor and the transmitter. Preferred are sensors that detect a plurality of different components in the gas and provide a distinct signal for each component. A preferred transmitter is designed to transmit at a low duty cycle so as to conserve power. A preferred sensor is electronic, has the capability for self-diagnostics and self-calibration, and causes a change in current when exposed to the component, such as a functionalized field effect transistor.

33 Claims, 1 Drawing Sheet

WIRELESS GAS COMPOSITION SENSOR SYSTEM

FIELD OF THE INVENTION

The present invention relates in general to a multi-component exhaust sensor system. More particularly, the present invention relates to a sensor system that employs a gas sensor, a thermopile as a source of power, and a wireless transmitter for transmitting the data sensed by the sensor.

BACKGROUND OF THE INVENTION

Multi-component exhaust gas sensors are needed to meet increasingly stringent government regulations. They are also needed for control of combustion performance and fuel economy. There is also a need for sensors that operate in other fluid streams, such as smoke stacks and other discharge media. However, presently available exhaust gas sensors are costly, consume a lot of power, and/or are often limited to sensing one component. Sensors are available that sense $O_2$ or $N_x$, but are typically not able to sense gases like CO, CO2, or $SO_2$. In addition, their high power consumption does not allow self-powered operation.

U.S. Patent Application No. 2004/0200900 to Hall discloses a sensing platform that can be used to accommodate new sensors and other electronics that Hall says are evolving so rapidly they are obsolete almost as they are developed. Paragraph 0169 suggests a thermopile, powered by a nuclear isotope. No specific mention of any self-powered sensor is made, nor is the idea of placing the platform in an exhaust system of a vehicle even possible.

U.S. Patent Application No. 2004/0226600 to Starer et al. operates a gas valve that is powered by a thermopile that derives heat from a pilot flame. The sensor does not seek to detect specific gases. U.S. Pat. No. 5,393,351 to Kinard et al. discloses a multilayer film multifunction thermal converter that uses thin films in combination with thermopiles and thermocouples. U.S. Pat. No. 5,576,251 to Garabedian et al. discloses a FET as a sensor but not for exhaust gases and not in combination with a thermopile for power or a transmitter for signal transmission.

Accordingly it would be of great advantage in the sensor art if a sensor could be provided that can measure all the various exhaust gas components.

Another advantage would be if a sensor could be developed that operates at sufficiently low power to be driven by a self-generated power source.

Yet another advantage would be to provide a sensor that would include self-diagnostics and self-calibration.

Still another advantage would be to provide a sensor that would operate with a wireless data transfer component.

Other advantages and features will appear hereinafter.

SUMMARY OF THE INVENTION

The present invention provides a sensor system and method for detecting the presence of at least one specific component in a fluid medium such as an exhaust gas. An exhaust gas, for the purposes of this invention may be the exhaust gas from a vehicle such as an automobile, or the exhaust gas in a chimney or other stack, or any other exhaust from combustion.

A sensor body is positioned proximate the fluid medium to mount a sensor for detecting the presence of at least one specific component and providing a signal representative of that presence. Preferred are sensors that detect a plurality of components in a medium. In exhaust gasses, for example, the sensor may detect $O_2$, CO, $CO_2$, $NO_x$, NO, $NO_2$, $SO_2$, $NH_3$, $CH_4$, and other combustion products.

The sensor may be a functionalized field effect transistor, a FFET, in which the gas analyte interacts with the gate material and changes its work function, or a functionalized $ZrO_2$ based sensor, which is also known as a solid-state electrochemical potentiometric sensor, or a micro discharge device that includes a microspectrometer. Other sensors that detect the presence of a sought out component in a fluid medium are also contemplated in the present invention. When a FFET is used, for example, it may be self-calibrated by injecting a voltage pulse to the FET gate, to induce a known but short work-function shift, which would give rise to a pre-determined signal output change.

Also provided is a transmitter for transmitting the signal from the sensor to a remote receiver for processing. The receiver may be combined with a control unit, such as one that adjusts the fuel to air mixture during combustion, or it may store data for use later, such as in determining the effectiveness of catalysts in exhaust systems.

A power source is used for powering the sensor and the transmitter. A preferred power source is a thermopile that generates current from the heat of the exhaust gas itself, and that power is stored, preferably in a capacitor, though a battery could be used.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
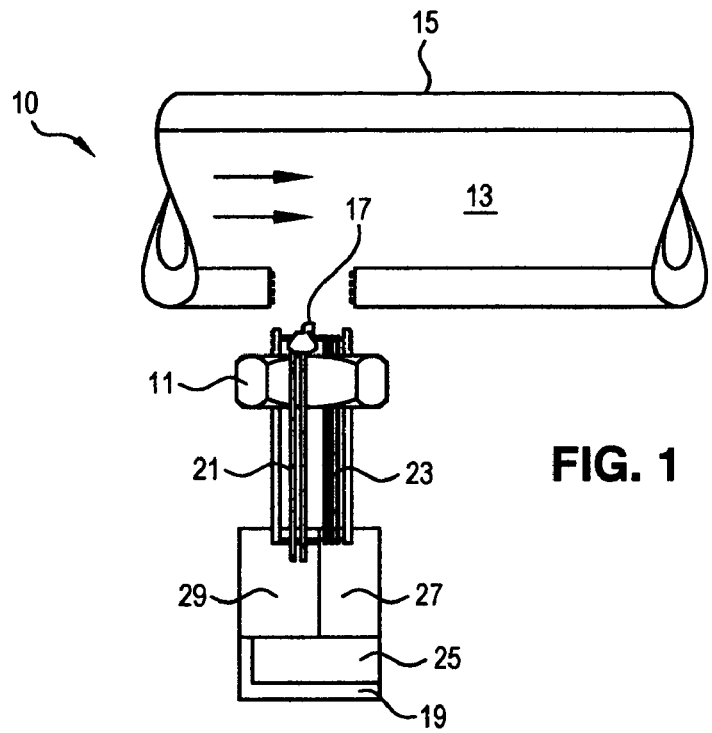
FIG. 1 is a side elevational view in cross section of an embodiment of the present invention.

The present invention is a sensor system for detecting the presence of at least one specific component in a fluid medium such as an exhaust gas. In it's simplest form, the present invention, as shown in FIG. 1 by 10 generally, includes a sensor body 11 positioned proximate a fluid medium 13 in exhaust or stack 15.

A sensor 17 is mounted in the sensor body 11 for detecting the presence of at least one specific component in the fluid and providing a signal representative of its presence. Preferred are sensors that detect a plurality of components in a medium. In exhaust gasses, for example, the sensor may detect $O_2$, CO, $CO_2$, $NO_x$, NO, $NO_2$, $SO_2$, $NH_3$, $CH_4$, and other combustion products. Also contemplated are sensors that detect the group of alkenes or even larger groups of organic materials.

A transmitter 19 is provided for transmitting the signal or signals to a remote receiver, not shown, for processing and use as desired. Also provided is a power source 21 for powering sensor 17 and transmitter 19. Power source 21 is, preferably, a thermopile 23 that obtains heat from medium 13 and stores electric energy in a power storage component 25. Power storage component 25 is preferably a capacitor of some form, such as a super-capacitor, though batteries and other electrical energy storage devices may also be used. It may be necessary to condition the energy from thermopile 23 by a power conditioning circuit 27. Electrical power is used both for the sensor 17 and for the transmitter 19, and the conditioning circuit 27. Depending upon the type of transmitter 19 that is employed, it may be necessary to convert the signal from the sensor 17 into some form more suitable for use by the transmitter 19, using a signal processing element 29. Signal processing element 29 may also be used to perform self-calibration of sensor 17.

The transmitter 19 is preferably designed to transmit at a low duty cycle so as to conserve power. For example, the transmitter might transmit data from as little as about 1 millisecond per second to 100 or more millisecond per second. Preferred transmission times are about 10 millisecond per second with the transmitter dormant for 990 millisecond per second, which is equivalent to a 1% duty cycle.

The sensor may be a functionalized field effect transistor, a FFET, featuring appropriate, tailored, proprietary films on FET gates, which cause measurable changes in the source-to-drain current when the targeted analyte gas absorbs or otherwise interacts with the gate material and changes its work function, or a functionalized $ZrO_2$ based sensor, which is also known as a solid-state electrochemical potentiometric sensor, or a micro discharge device, which consists of about a 0.1 mW discharge and a microspectrometer. Other sensors that detect the presence of a sought out component in a fluid medium are also contemplated in the present invention. Presented below in Table I are exemplary film materials for FFET gates that may selectively interact with individual target analytes.

TABLE I

| Analyte | Film | Reversible Reaction Product |
|---------|------|------------------------------|
| CO | Fe | $Fe(CO)_5$ |
| CO | Ni | $Ni(CO)_5$ |
| $CO_2$ | CaO | $CaCO_3$ |
| $CO_2$ | NaO | $NaCO_3$ |
| $H_2$ | Pd/Ni | $Pd/Ni.H_2$ |
| $O_2$ | | |
| $NH_3$ | $CoCl_{12}$ | $Co(NH_3)_6Cl_{12}$ |
| $NH_3$ | $FeCl_{13}$ | $Fe(NH_3)_6Cl_{13}$ |
| $NH_3$ | $NiCl_{12}$ | $Ni(NH_3)_6Cl_{12}$ |
| NO | | |
| $NO_2$ | | |
| $SO_2$ | | |

Figure 2:
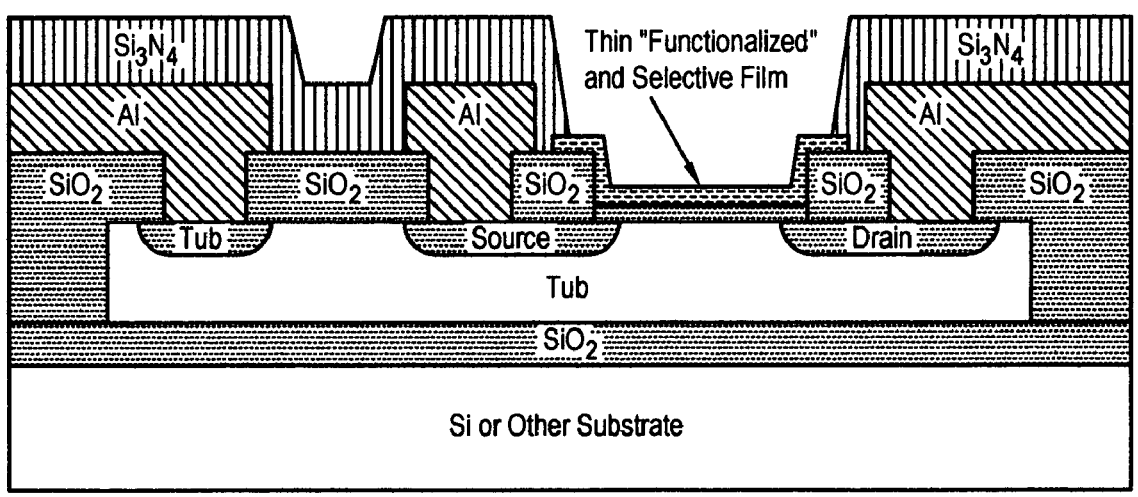
FIG. 2 is a side elevational view in cross section of a sensor used in an embodiment of the present invention.

FIG. 2 shows the cross section of a typical FFET and the location between source and drain of the selective, functionalized film. There would be one such FFET for each analyte, but several such FFET's could form a monolithic mosaic-like cluster on one chip. Alternatively, several chips could be mounted close together to utilize the same power source and transmitter. The main distinction among the different FFETs may be the different materials serving to differentiate and make each FFET in the cluster selectively sensitive to one of the target analytes.

Self-calibration of the various FFETs may be achieved by injecting a voltage pulse to the FET gate, to induce a known but short work-function (potential) shift, which may give rise to a pre-determined signal output change. The reference signal for all of the sensors may be obtained (and compared with stored data) when the combustion system or other fluid source is not operating. This provides an air-sample to the sensor system. It is also useful to monitor the response of the sensor when exposed to air, while the combustion system is not in operation. The output signal can then be adjusted as needed.

While particular embodiments of the present invention have been illustrated and described, they are merely exemplary and a person skilled in the art may make variations and modifications to the embodiments described herein without departing from the spirit and scope of the present invention. All such equivalent variations and modifications are intended to be included within the scope of this invention, and it is not intended to limit the invention, except as defined by the following claims.

The invention claimed is:

1. A sensor system for detecting the presence of at least one specific component in an exhaust gas having an elevated temperature, comprising:
   a sensor body positioned proximate said exhaust gas;
   a sensor mounted in said sensor body for detecting the presence of at least one specific component and providing a signal representative of said presence;
   a wireless transmitter for transmitting said signal to a remote receiver for processing; and
   a power source including a thermopile and a power storage element wherein heat from said exhaust gas causes said thermopile to transmit power to said power storage for powering said sensor and said transmitter.

2. The system of claim 1, where said power storage is a capacitor.

3. The system of claim 1, where said power storage is a battery.

4. The system of claim 1, where said power source is a solar cell.

5. The system of claim 1, where said sensor is adapted to detect the presence of a plurality of components in said gas and provide a distinct signal for each of said plurality of different components when present in said gas.

6. The system of claim 1, wherein said transmitter transmits said signal intermittently in a low duty cycle.

7. The system of claim 6, where said transmitter transmits for about 10 millisecond per second.

8. The system of claim 1, where said sensor is an electronic sensor that causes a change in current when exposed to said at least one component.

9. The system of claim 8, where said sensor is selected from the group consisting of a functionalized field effect transistor, a solid-state electrochemical potentiometric sensor, a microdischarge system with a microspectrometer.

10. The system of claim 9, where said sensor is a functionalized field effect transistor.

11. The system of claim 10, where said sensor includes self-diagnostics and self-calibration caused by injection of a voltage pulse to the FET gate to induce a short but known work-function level.

12. A sensor system for detecting the presence of at least one specific component in an exhaust gas having an elevated temperature, comprising:
   a sensor body positioned proximate said exhaust gas;
   sensor means mounted in said sensor body for detecting the presence of at least one specific component and providing a signal representative of said presence;
   wireless transmitter means for transmitting said signal to a remote receiver for processing; and
   power source means including a thermopile wherein heat from said exhaust gas causes said thermopile to transmit power and a power storage means for storing said power for powering said sensor means and said transmitter means.

13. The system of claim 12, where said power storage means is a capacitor.

14. The system of claim 12, where said power storage means is a battery.

15. The system of claim 12, where said power source means is a solar cell.

16. The system of claim 12, where said sensor means is adapted to detect the presence of a plurality of components in said gas and provide a distinct signal for each of said plurality of different components when present in said gas.

17. The system of claim 12, wherein said transmitter means transmits said signal in a low duty cycle.

18. The system of claim 17, where said transmitter means transmits for about 10 millisecond per second.

19. The system of claim 12, where said sensor means is an electronic sensor that causes a change in current when exposed to said at least one component.

20. The system of claim 19, where said sensor means is selected from the group consisting of a functionalized field effect transistor, a solid-state electrochemical potentiometric sensor, a microdischarge system with a microspectrometer.

21. The system of claim 20, where said sensor means is a functionalized field effect transistor.

22. The system of claim 21, where said sensor means includes self-diagnostics and self-calibration caused by injection of a voltage pulse to the FET gate to induce a short but known work-function level.

23. A method for detecting the presence of at least one specific component in an exhaust gas having an elevated temperature, comprising the steps of:
   placing a sensor body positioned proximate said exhaust gas;
   detecting the presence of at least one specific component with a sensor mounted in said sensor body and providing a signal representative of said presence;
   wirelessly transmitting said signal to a remote receiver for processing; and
   powering said sensor and said transmitter with a power source including a thermopile transmitting power from the heat from said exhaust gas to a power storage element in said sensor body.

24. The method of claim 23, where said power storage element is a capacitor.

25. The method of claim 23, where said power storage element is a battery.

26. The method of claim 23, where a solar cell transmits power to a power storage element in said sensor body.

27. The method of claim 23, where said sensor is adapted to detect the presence of a plurality of components in said gas and provide a distinct signal for each of said plurality of different components when present in said gas.

28. The method of claim 23, wherein said transmitter transmits said signal intermittently in a low duty cycle.

29. The method of claim 28, where said transmitter transmits for about 10 millisecond per second.

30. The method of claim 23, where said sensor is an electronic sensor that causes a change in current when exposed to said at least one component.

31. The method of claim 30, where said sensor is selected from the group consisting of a functionalized field effect transistor, a solid-state electrochemical potentiometric sensor, a microdischarge method with a microspectrometer.

32. The system of claim 31, where said sensor is a functionalized field effect transistor.

33. The system of claim 32, where said sensor includes self-diagnostics and self-calibration caused by injection of a voltage pulse to the FET gate to induce a short but known work-function level.

* * * * *